United States Patent [19]

Murnick

[11] Patent Number: 5,394,236
[45] Date of Patent: Feb. 28, 1995

[54] METHODS AND APPARATUS FOR ISOTOPIC ANALYSIS

[75] Inventor: Daniel E. Murnick, Bernardsville, N.J.

[73] Assignee: Rutgers, The State University, Piscataway, N.J.

[21] Appl. No.: 829,416

[22] Filed: Feb. 3, 1992

[51] Int. Cl.[6] ............................................. G01J 3/30
[52] U.S. Cl. .................................. 356/311; 356/308; 356/315
[58] Field of Search ........................ 356/311, 308, 315

[56] References Cited

U.S. PATENT DOCUMENTS

| | | | |
|---|---|---|---|
| 4,184,127 | 1/1980 | Green et al. | 356/308 X |
| 4,402,606 | 9/1983 | Zalewski et al. | 356/315 |
| 4,684,805 | 8/1987 | Shu-Ti Lee et al. | 250/343 |
| 4,707,133 | 11/1987 | Roberts et al. | 356/320 |
| 4,968,887 | 11/1990 | Wong | 250/343 |

FOREIGN PATENT DOCUMENTS

| | | |
|---|---|---|
| 294634 | 10/1991 | Germany. |
| 9110895 | 7/1991 | WIPO. |
| 9315391 | 8/1993 | WIPO. |

OTHER PUBLICATIONS

"Carbon Dioxide Laser" pp. 2–5 of Laser Processing published by National Science Council of Executive Yuan (Republic of China), May 1987.

"Glow Discharge Mass Spectrometry" (GOMS), pp. 57–58, vol. 73 of Latest Information of Scientific Apparatus published by National Science Council of Executive Yuan (Republic of China), Apr. 1993.

Lee-High Resolution Infrared Diode Laser Spectroscopy for Isotope Analysis Measurement of Isotopic Carbon Monoxide, *Applied Physics Letters*, 48 (10), 10 Mar. 1986, pp. 619–621.

Gagne et al.-Effet Optogalvanique Dans Une Decharge a Cathode Creuse: Mechanisme et Dosage Isotopique de L'araniun, *Journal de Physique*, C7, No. 11 vol. 44, pp. C7-355 to C7-369 (Nov., 1983) & English translation.

Keller, et al.-Optogalvanic Spectroscopy in a Uranium Hollow Cathode Discharge, *Opt. Soc. Am.*, vol. 69, No. 5, May 1979, pp. 738–742.

Aerodyne Research, Inc. "A Carbon–13 Isotope Analyzer", NSF Grant No. ISI 88–60778, Abstracts of Phase I Awares, NSF Small Business Innovation Research Program, Nov. 1989.

"New Laser Spectroscopic Technique for Stagle–Isotope Ratio Analysis" by William G. Tong, Dec. 1984 (Ph.D. thesis submitted to Iowa State University).

IEEE Journal Of Quantum Electronics, vol. QE-22, No. 2, Feb. 1986, Entitled, "Absolute Frequencies Of Lasing Transitions In Nine $CO_2$ Isotopic Species, By L. C. Bradley, K. L. Soohoo, and C. Freed" Ames Laboratory, Iowa State University, Ames, Iowa 50011, Dec., 1984.

"New Laser Spectroscopic Technique For Stable–Isotope Ratio Analysis By William G. Tong" PhD Thesis submitted to Iowa State University.

*Primary Examiner*—Vincent P. McGraw
*Assistant Examiner*—K. P. Hantis
*Attorney, Agent, or Firm*—Lerner, David, Littenberg, Krumholz & Mentlik

[57] ABSTRACT

The isotopic composition of a multiatomic isotope-bearing species such as $CO_2$ in an analyte is measured by maintaining the analyte in a condition such that isotope-bearing species are present in an excited state and directing light at wavelengths corresponding to transition energies of isotope-bearing species with different isotopes. The interaction between the analyte and light at the different wavelengths is monitored, as by monitoring the optogalvanic effect caused by the light of the different wavelengths. The light may be supplied by a laser including the isotope-bearing species. A stable isotope such as $^{13}C$ or $^{18}O$ can be used as a tracer in a chemical or biological test and detected using the composition-determining method.

16 Claims, 2 Drawing Sheets

METHODS AND APPARATUS FOR ISOTOPIC ANALYSIS

FIELD OF THE INVENTION

The present invention relates to the field of isotopic analysis and to the field of testing using tracer isotopes.

BACKGROUND OF THE INVENTION

It is often necessary to determine the amounts of different isotopes in a material. Isotopes are different forms of the same chemical element, having nuclei of different masses. For example, naturally occurring carbon consists predominantly of $^{12}C$, i.e., carbon having an atomic mass of 12 atomic mass units with small amounts of the $^{13}C$ and $^{14}C$ isotopes, having atomic masses of 13 and 14 AMU respectively. The $^{12}C$ and $^{13}C$ isotopes are stable, whereas the $^{14}C$ isotope is radioactive, and spontaneously decays to other elements with time. In so-called "carbon dating", the ratio of $^{14}C$ to $^{12}C$ in a specimen is measured to obtain an indication of the age of the specimen. Numerous biological and chemical tests use radioactive tracers such as $^{14}C$. A carbon-containing compound which interacts with a biological or chemical system such as a living organism is prepared using $^{14}C$ in place of naturally occurring carbon, so that the compound is "labelled" or "tagged" with the $^{14}C$. The biological specimen is then exposed to the labelled compound so that the specimen interacts with the labelled compound. This interaction produces a test specimen or analyte incorporating $^{14}C$ from the labelled compound, in amounts directly related to the biological interaction of interest. For example, in radio immunoassay tests, the amounts of a particular antibody in a biological specimen can be measured by exposing the specimen to a $^{14}C$-labelled antigen adapted to bind chemically with the antibody. The amount of antigen taken up by the specimen, and hence the amount of $^{14}C$ taken up by the specimen, provides a measure of the amount of antibody in the specimen. In other tests, the specimen may be a substance excreted or exuded by the biological specimen. For example, $^{14}C$-labelled urea may be administered to a living mammalian subject such as a human being. If certain bacteria are present in the subjects intestinal tract, the carbon dioxide exhaled in the subject's breath will include the labelling isotope incorporated in the urea. Thus, such bacteria can be detected by monitoring the ratio of $^{14}C$ to $^{12}C$ in the subject's breath.

$^{14}C$ is ordinarily used as the labelling isotope in these and other tests because it can be detected by monitoring the radiation which it emits when it decays. Such monitoring may be performed using relatively simple instruments. However, the use of radioactive materials is undesirable. Such radioactive materials are inherently unstable. Moreover, although the amounts of radioactive materials used in tracer studies of this nature typically are small, any radioactivity is undesirable with respect to safety and health considerations. In theory, directly analogous tracer studies can be performed using the stable, rare isotope $^{13}C$ as the labelling isotope instead of $^{14}C$. However, it is difficult to measure the amount of $^{13}C$ or the ratio of $^{13}C$ to $^{12}C$ in a sample. Such measurements typically have been performed heretofore using mass spectrometers. The cost and complexity associated with mass spectrometry pose significant drawbacks. Moreover, mass spectrometry is unusable in certain situations. Mass spectrometry cannot distinguish between different chemical species having the same mass. Great care must be taken to eliminate background atoms, molecules and radicals having the same mass as the species of interest. Accordingly, there has been a long-felt need for improved methods of measuring the amounts of carbon isotopes in an analyte.

There have been corresponding needs for improved methods of measuring the amounts of isotopes of other elements in analytes. For example, a method of measuring the amount of the rare but stable oxygen isotope $^{18}O$, and/or the ratio of $^{18}O$ to the common isotope $^{16}O$ would be highly desirable. This need is particularly acute because ordinary water molecules ($H_2O$) have essentially the same mass. (18 AMU) as $^{18}O$ atoms. It is ordinarily impractical to measure the $^{18}O:^{16}O$ ratio of a sample containing even a trace amount of water by mass spectroscopy, particularly where the ratio $^{18}O:^{16}O$ is small. The $^{18}O$ signal is simply overwhelmed by the signal arising from water in the sample. Apparently for this reason, $^{18}O$ has not been widely used as a tracer in chemical and biological studies. Similar needs exist with respect to other elements.

Various attempts have been made to determine the amounts of isotopes in samples by spectroscopic techniques, i.e., by measuring the response of the sample to applied radiant energy. It has long been known that the energy absorption spectrum of atoms of different isotopes differ from one another, and some work has been done towards exploiting these differences for monitoring the isotopic composition of an analyte. As set forth in Lee, High Resolution Infrared Diode Laser Spectroscopy for Isotope Analysis—Measurement of Isotopic Carbon monoxide, *Applied Physics Letters*, 48 (10), Mar. 10, 1986, pp. 619–621, a light beam from a tunable diode laser can be directed through a sample of carbon monoxide to a photodetector. The laser is tuned in succession to different wavelengths. Each such wavelength corresponds to a ground-state absorption wavelength of a carbon monoxide molecule containing a particular isotope of oxygen. The amount of light absorbed and hence the amount of light detected at each of these wavelengths is related to the amount of the particular oxygen isotope present in the carbon monoxide. This system, however, requires complex and highly sensitive instrumentation. The wavelengths absorbed by the different isotopic forms of CO are extremely close to one another, within the range of about 2119.581–2120.235 $cm^{-1}$. To provide for precise tunability within this range, a so-called quantum well diode laser is employed. Such a laser must be operated at liquid nitrogen temperatures, and provides only a very weak signal, which in turn requires a large and complex liquid nitrogen cooled photo detector. Accordingly, this method has not been widely adopted.

Keller et al, Optogalvanic Spectroscopy in a Uranium Hollow Cathode Discharge, *Opt. Soc. Am.*, Vol 69, No. 5, May 1979, pp. 738–742, discloses a spectroscopic method in which uranium metal is subjected to sputtering in a hollow cathode discharge. The discharge thus includes sputtered uranium atoms in the ground or unexcited state. This electrical discharge is subjected to irradiation by a laser at varying wavelengths. The interaction between the laser light and the discharge is monitored by monitoring the so-called optogalvanic effect, i.e., the change in the electrical impedance of the discharge upon irradiation. The optogalvanic effect produced by light at a so-called "hyperfine" absorption wavelength of $^{238}U$ atoms is compared with the optogalvanic effect at a hyperfine absorption wavelength of $^{235}U$. This provides a measure of the isotopic ratio $^{235}U/^{238}U$. A generally similar approach is set forth in Gagne et al, Effet Optogalvanique Dans Une Decharge a Cathode Creuse: Mechanisme et Dosage Isotopique de l'araniun, *Journal de Physique*, C7, No. 11, Vol. 44, pp. C7–355 to C7–369 (November, 1983).

Another similar approach to the analysis of copper isotopes $^{63}Cu$ and $^{65}Cu$ is disclosed in Tong, New Laser Spectroscopic Technique for Stable-isotope Ratio Analysis, PhD. thesis, Iowa State University, Ames, Iowa December 1984, U.S. DOE report IS-T-1156. This thesis uses the optogalvanic effect to monitor hyperfine spectral components of optical absorption in an electrical discharge containing copper atoms. This approach requires a subsequent deconvolution step to obtain an estimate of the $^{63}Cu$ and $^{65}Cu$ components. Tong suggests that the technique could be used in conjunction with Cu-based tracer studies, as, for example, using a stable copper isotope as a tracer to study copper metabolism. A transition from a ground state of the copper atom is employed. The reference also states that it is "feasible" to observe the optogalvanic effect in transitions of the atoms originating from excited states as well as from ground states, but merely suggests that this allows one to choose "an appropriate excitation wavelength where there is minimal spectral interference." Attempts to monitor the hyperfine absorption of metal atoms, however, encounter serious drawbacks. The hyperfine spectra of the various isotopes include closely-spaced and overlapping absorption wavelengths so that complex equipment and mathematical deconvolution techniques are required to segregate the effects due to absorption by the different isotopes in the analyte.

A published summary of a grant application by Aerodyne Research, Inc., entitled "A Carbon-13 Isotope Analyzer", NSF Grant No. ISI 88-60778, Abstracts of Phase I Awards, NSF Small Business Innovation Research Program (SBIR) 1989, National Science Foundation, November 1989 describes a planned attempt to determine the $^{13}C:^{12}C$ isotopic ratio of carbon monoxide by imaging the emission spectrum of a CO plasma and applying so-called "spectral processing algorithms" to suppress interference arising from various sources. This approach has not gained wide acceptance.

Thus, in spite all of this effort in the art heretofore, there have still been significant unmet needs for improved methods of isotopic analysis. The need for improved methods and apparatus applicable to relatively low atomic number elements such as carbon, nitrogen, oxygen and hydrogen has been particularly acute.

SUMMARY OF THE INVENTION

The present invention addresses these needs.

One aspect of the present invention provides methods of determining the isotopic composition of an analyte which includes isotope-bearing species incorporating plural different isotopes. A method according to this aspect of the present invention preferably includes the step of providing the analyte in a condition such that at least some of the isotope-bearing species in the analyte are present in excited states. In these excited states, at least some electrons are at energy levels higher than the energy levels occupied in the ground or normal state of the isotope-bearing species. For each such excited state, there are transition energies. Each such transition energy corresponds to the energy released upon transition from the excited state to a lower state or absorbed upon transition from the excited state to a still higher-energy excited state. The transition energies are different for isotope-bearing species incorporating different isotopes. The method further includes the step of applying electromagnetic radiation such as light to the analyte at plural wavelengths corresponding to transition energies of the excited isotope-bearing species including the various isotopes. That is, the wavelengths in the applied light are selected so that at one such wavelength, each photon in the applied light has energy equal to a transition energy of an excited species including one isotope, whereas at another applied wavelength each photon has energy equal to the transition energy of an excited species including another isotope. Accordingly, light at each applied wavelength will interact substantially only with species including one isotope. The method further includes the step of monitoring response of the analyte to the applied radiation so as to determine the magnitude of such response for each of the applied wavelengths.

Most preferably, the isotope-bearing species incorporated in the analyte are multi-atomic moities such as molecules and multi-atomic ions. The multi-atomic species have discrete, well separated transition energies. The applied radiation can be produced by a laser locked to the particular transition energy in question. In a particularly preferred arrangement, the step of applying radiation includes the step of operating at least one laser having at least one lasing medium incorporating the isotope-bearing species. The laser or lasers will be inherently locked to the transition wavelengths of the isotope bearing species. In a particularly preferred method, the light is applied by operating a single laser having a single lasing medium including the isotope-bearing species having the plural different isotopes, and this single laser is actuated to emit the different wavelengths corresponding to the different transition energies sequentially. For example, the isotope-bearing species in the analyte may be $CO_2$ molecules including different carbon isotopes and the light may be applied by actuating a gas laser having a gaseous lasing medium including $CO_2$ with the various isotopes and tuning the laser to emit wavelengths associated with different isotopes sequentially.

Most preferably, the analyte is provided in gaseous form in an electrical discharge so that the discharge maintains the isotope-bearing species in the excited states. The step of monitoring the response of the analyte desirably includes the step of monitoring a non-optical phenomenon such as the electrical impedance of the discharge. Thus, response of the analyte to the applied light may be monitored by observing the optogalvanic effect. The excited state of the isotope-bearing species tends to provide substantially enhanced response. In particular, the optogalvanic effect can be measured far more readily in an excited-state analyte than in a ground-state analyte. The responses at the various wavelengths can be used directly, or preferably, the magnitude of these responses can be ratioed to provide a measure of the ratio of isotopic concentrations in the analyte.

Preferred methods according to this aspect of the invention can be used to determine the isotopic ratio of elements such as carbon, oxygen, nitrogen and hydrogen, or the abundance of various isotopes in an analyte.

In particularly preferred methods, the isotope bearing species is selected from the group consisting of oxides of carbon, oxides of nitrogen, diatomic nitrogen, water vapor and combinations thereof. Carbon dioxide is an especially preferred isotope-bearing species. Most preferably, the various isotopes analyzed are stable, non-radioactive isotopes.

Methods according to further aspects of the present invention include the further step of deriving the analyte from a test subject so that the amounts of the various isotopes vary depending upon a characteristic of the test subject. Thus, the magnitudes of the responses for the different wavelengths will provide an indication of the characteristic of the test subject. In particularly preferred arrangements, the test subject is a living organism, and the step of deriving the analyte includes the step of exposing the organism to at least one reagent containing one of the isotopes. Stable isotopes are particularly preferred in methods according to this aspect of the invention. Preferred methods according to this aspect of the invention allow the use of stable isotopes as tracers in tests which heretofore utilized radioactive tracers.

Further aspects of the present invention provide apparatus for determining the isotopic composition of an analyte. Apparatus according to this aspect of the invention most preferably includes means for providing the analyte in a condition so that isotope-bearing species in the analyte are present in excited states, whereby excited isotope bearing species incorporating different isotopes will have different transition energies. The apparatus most preferably further includes means for applying electromagnetic radiation to the analyte at plural wavelengths corresponding to the different transition energies and means for monitoring response of the analyte to the applied radiation so as to determine the magnitude of such response for each of the various wavelengths provided by the radiation-applying means. Most preferably, the means for providing the analyte includes means for maintaining an analyte including a multi-atomic isotope-bearing species in a gaseous, excited state. This means may include means for maintaining the electrical discharge in the analyte. The means for monitoring response of the analyte may include means for monitoring the electrical impedance of the discharge. The radiation-applying means may include one or more lasers including at least one lasing medium incorporating the isotope-bearing species. Apparatus according to this aspect of the invention can be used to practice the methods discussed above.

These and other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 2:
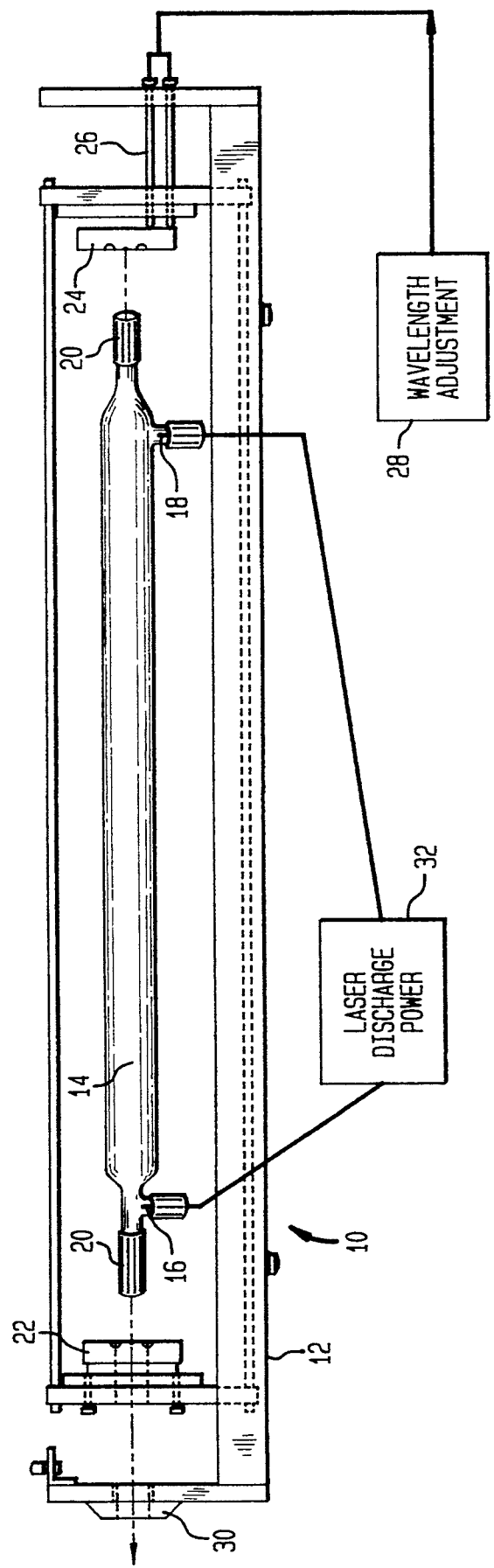
FIG. 2 is schematic sectional view of a laser incorporated in the apparatus of FIG. 1.

Apparatus in accordance with one embodiment of the present invention includes a laser 10. As illustrated in FIG. 2, laser 10 incorporates a housing 12 and an elongated discharge tube 14 mounted within the housing. A pair of discharge electrodes 16 and 18 area connected to the space within tube 14. A discharge tube has Brewster or polarizing windows 20 at both ends. A partially reflective output mirror 22 is positioned adjacent a first or output end of tube 14 in alignment with window 20. Output mirror 22 is provided with conventional adjusting devices for precisely aligning the output mirror in a desired plane. A diffraction grating 24 is pivotally mounted to housing 12 adjacent the second end of tube 14, opposite from output mirror 22. Grating 24 is connected to adjustment screws 26 so that the grating can be tilted relative to the axis of tube 14 by action of the adjustment screws. Adjustment screws 26 in turn are linked to a wavelength adjustment unit 28 arranged to report the position of the screws and hence the position of the grating to an external control device. The housing 12 has an opening 30 aligned with the axis of tube 14 at the output end. A laser discharge power supply 32 is connected to electrodes 16 and 18 for providing an electrical discharge within tube 14. The foregoing elements of laser 10 may conform to the conventional principles of construction and operation used with tunable gas-discharge lasers. In the conventional fashion, grating 24 diffracts light incidence upon it to different wavelengths at different angles relative to the plane of the grating. By adjustment of screws 26, grating 24 can be positioned so that when a light beam containing a particular wavelength is directed along the axis of tube 14 through window 20 to the grating, light of a particular wavelength will be selectively diffracted back along the axis of the tube whereas other wavelengths will be diffracted off-axis.

Tube 14 is filled with a gas mixture containing about 9 percent $CO_2$ in admixture with about 80 percent He and about 11 percent $N_2$. The gas mixture is under about 6 torr absolute pressure. The carbon dioxide molecules in the gas mixture have an abnormal carbon isotope composition. As used in this disclosure with reference to an element, the term "abnormal isotope composition" means a proportion of isotopes different from the proportion in naturally occurring terrestrial sources of the element. In particular, the ratio of $^{13}C$ to $^{12}C$ in the carbon dioxide of the gas mixture is far higher than in naturally occurring $CO_2$ on earth. Preferably, the $CO_2$ in the gas mixture includes at least about 10 percent $^{13}C$ and more preferably at least about 40 percent, most preferably between about 40 percent and about 60 percent $^{13}CO_2$, the remainder consisting essentially of $^{12}CO_2$. The oxygen in the $CO_2$ has the normal isotope composition, and hence consists essentially of $^{16}O$.

Figure 1:
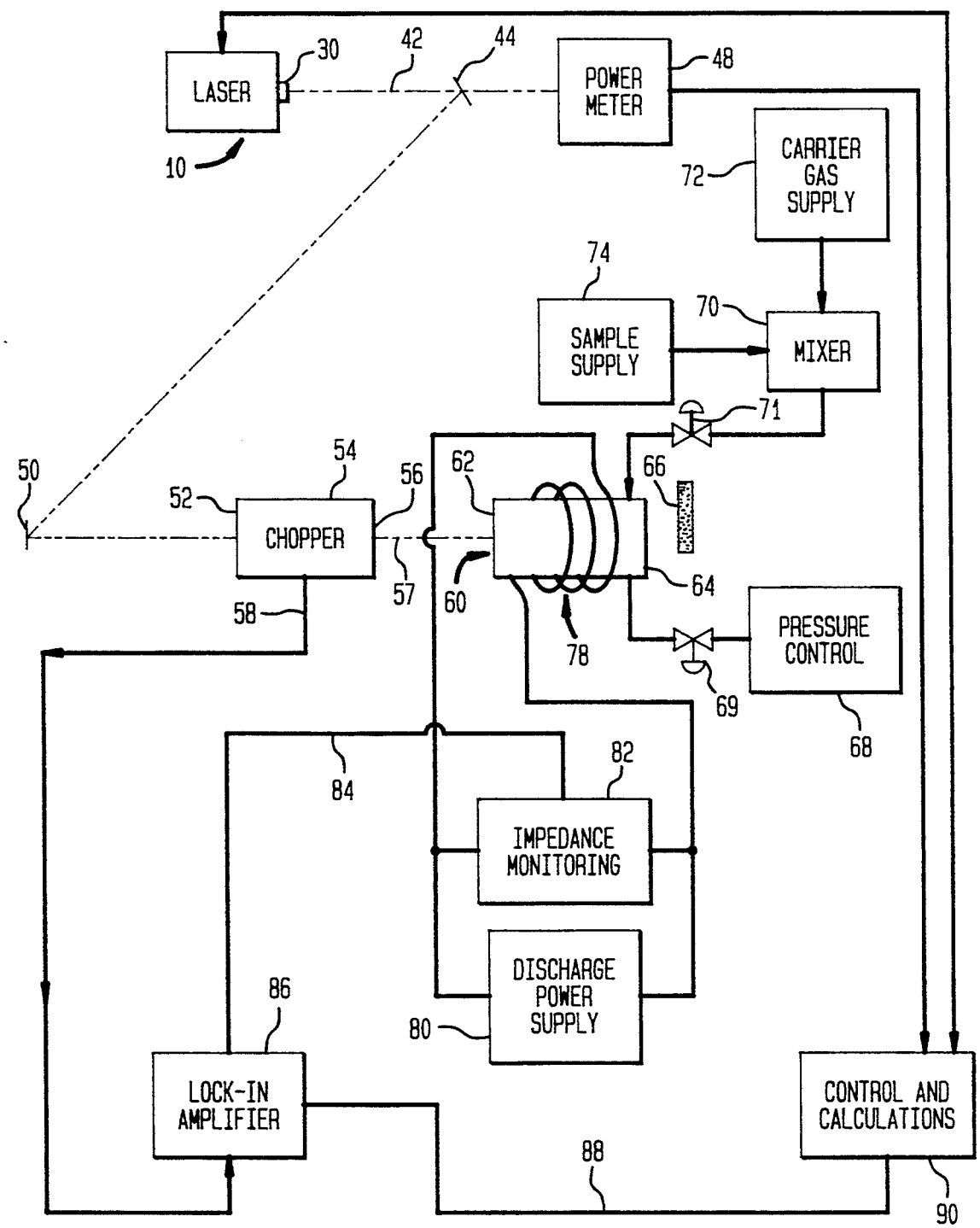
FIG. 1 is a block diagrammatic view of apparatus in accordance with one embodiment of the present invention.

Laser 10 is employed with the other elements shown in FIG. 1. The output opening 30 of the laser is directed along a first beam path 42 to a partially reflective mirror 44. Mirror 44 is arranged to reflect the major portion of the light along a further beam path 46, and to allow a minor, fixed proportion of the light to pass through the mirror to the input of a light power meter 48. The beam path 46 continues via a fully reflective mirror 50 to the light input 52 of an optical chopper 54. Chopper 54 is a controllable shutter device arranged to interrupt the light beam entering through input 52 at a preselected frequency and to direct the chopped or interrupted beam out through a light output opening 56, along path 57. Chopper 54 also has an electrical signal output 58. The chopper is arranged to provide a first signal at output 58 when the light is not interrupted and a second, different signal when the light is interrupted. A sample cell 60, formed from a dielectric material and having transparent end walls 62 and 64 is disposed between the light output 56 of chopper 54 and a fully reflective mirror 66. Sample cell 60 desirably is a hollow tubular container defining a sample path length of at least about 3 cm between end walls 62 and 64. Cell 60 desirably has an interior volume less than about 100 cm$^3$ and more preferably less than about 10 cm$^3$. The end walls are formed from a dielectric material transparent to the light to be used in the measurement process, zinc selenide being preferred. The sample cell 60 and mirror 66 are arranged so that light discharged through the light outlet 56 of chopper 54 on path 57 is directed through the end walls and through the interior of the sample chamber to mirror 66 and reflected back by mirror 66 into the interior of the sample chamber through end wall 64.

The interior space within sample cell 60 is connected through a shut-off valve 69 to a pressure control apparatus 68, which may include a conventional arrangement of a vacuum pump and a pressure sensor (not shown). The interior of sample cell 60 is linked through a further shut-off valve 71 to a gas mixer 70, which may include a conventional mixing manifold. Mixer 70 is linked to a carrier gas supply unit 72, which includes conventional storage tanks holding the desired carrier gases, together with pressure and flow regulators. Mixer 70 is also linked to a sample supply unit 74 holding a sample of the analyte to be studied. Sample supply means 74, carrier gas supply means 72 and mixer 70 are arranged so that a gas mixture including any desired proportion of analyte and carrier gases can be provided through isolation valve 71 while the isolation valve is open, to thereby fill the interior of chamber 60 with these mixed gases.

An inductive coil 78 is in approximity to cell 60. The shape and size of the coil is selected so that an electrical discharge can be maintained between the gases present within cell 60 upon application of a reasonable electric field by induction through the coil.

Coil 78 is connected to a discharge power supply 80 arranged to supply radio-frequency or "RF" electrical power to the coil 78. The so-called "ISM" frequencies (those allocated by government radio spectrum authorities for industrial, scientific and medical use) are preferred, with frequencies of about 10 to about 20 MHz being particularly preferred. However, other frequencies can be used. DC (0 frequency) can be employed provided that coil 78 is replaced by an appropriate set of electrodes. An impedance monitoring device 82 is also linked to coil 78 and power supply 80. The impedance monitoring device is arranged to provide an electrical signal on output line 84 representing the electrical impedance of the space within the coil and hence representing the electrical impedance of the gasses within cell 60. The particular arrangement of impedance monitoring device 82 will depend upon the configuration of discharge power supply 80. In a typical impedance monitoring arrangement, the current drawn by the power supply to maintain the discharge is monitored. Various arrangements for monitoring the electrical impedance of a discharge are wellknown to those skilled in the discharge systems art, and any such arrangement can be employed.

Signal output line 84 of the impedance monitoring device is connected to a signal input of a lock-in amplifier 86. Lock-in amplifier 86 is also connected to the electrical signal output 58 of chopper 84. The lock-in amplifier is arranged to selectively amplify that component of the signal on line 84 which is in synchronism with the signal on line 58. That is, the lock in amplifier will selectively amplify only a component of the impedance signal on line 84 which varies in synchronism with the action of the chopper and hence in synchronism with the on and off cycling of the light beam on path 57. The lock-in amplifier thus will provide an oscillating signal varying between first and second extreme values at a frequency corresponding to the chopping frequency of chopper 54. This oscillating signal represents the component of the impedance which varies in response to the light passing along light path 57. Those components of the impedance which do not vary in accordance with the applied light are excluded from this oscillating signal. The lock-in amplifier provides the average magnitude of the oscillating signal as an output signal.

The output signal from the lock-in amplifier is passed along output line 88 to a control and calculation computer 90. Computer 90 is also linked to power meter 48 to receive light power readings from the power meter. The control and calculation computer also is linked to the laser discharge power source 32 (FIG. 2) of laser 10 so that computer 90 can control the discharge power. Also, the control and calculation device is linked to wavelength adjustment unit 28 (FIG. 2) of the laser so that computer 90 receives a signal denoting the particular wavelength being applied at all times. The computer is also provided with conventional input/output devices such as a keyboard, screen and printer (not shown) so that the user may supply control instructions and receive the results.

In a method according to one element of the invention, an analyte containing carbon dioxide and including both ordinary $^{12}CO_2$ and $^{13}CO_2$ is provided in sample supply means 74. The analyte is mixed with nitrogen to provide $N_2:CO_2$ molar ratio of about 20:1. The gas mixture is supplied through shut-off valve 71 to chamber 60, and the vacuum pump of pressure control apparatus 68 is actuated to bring the pressure within chamber 60 to a reasonable value for operation of a glow discharge, preferably less than about 15 torr, more preferably less than about 5 torr and most preferably between about 3 and about 5 torr. When the pressure is at the desired value, valves 71 and 69 are shut to thereby isolate the interior of chamber 60. Discharge power supply 80 is actuated to apply RF energy to the gas contained within cell 60, thereby creating an electrical discharge. The discharge raises a significant fraction of the $CO_2$ molecules in cell 60 to excited states, i.e., states having a higher energy than the normal or ground state. That is, the $CO_2$ molecules in the discharge are not in thermodynamic equilibrium but instead are in high-energy metastable or unstable states. Laser discharge power unit 32 (FIG. 2) is actuated to provoke a discharge within laser tube 14, thereby bringing the mixed gases in the laser tube to similar excited states.

$CO_2$ molecules in each excited state can undergo only discrete, quantized transitions to lower or higher energy states. Each such transition corresponds to emission or absorption of a particular quantum of energy. Thus, upon each such transition a photon having that particular amount of energy is emitted or absorbed. A photon having a particular amount of energy has a particular wavelength. Accordingly, each transition is associated with a particular wavelength and the $CO_2$ molecules in the glow discharge within laser tube 14 will emit only particular, discrete wavelengths, each such discrete wavelength being associated with one transition. The transition energies and hence transition wavelengths for $^{13}CO_2$ molecules differ significantly from the transition wavelengths for $^{12}CO_2$ molecules. Some of the significant transition wavelengths are shown in Table I below.

TABLE I
Certain Transition Wavelengths for $^{13}CO_2$ and $^{12}CO_2$

| BAND I LINES | WAVELENGTH (MICRONS) | |
|---|---|---|
| | $^{13}CO_2$ | $^{12}CO_2$ |
| P(12) | 11.06 | 10.51 |
| P(14) | 11.08 | 10.53 |
| P(16) | 11.10 | 10.55 |
| P(18) | 11.12 | 10.57 |
| P(20) | 11.15 | 10.59 |
| P(22) | 11.17 | 10.61 |
| P(24) | 11.19 | 10.63 |
| P(26) | 11.22 | 10.65 |
| P(28) | 11.24 | 10.67 |
| P(30) | 11.26 | 10.70 |

As the gas mixture in tube 14 contains both $^{13}CO_2$ and $^{12}CO_2$, the gas mixture in the laser tube will undergo both the $^{13}CO_2$ and the $^{12}CO_2$ transitions and hence would tend to emit light at the wavelengths corresponding to both sets of transitions.

Depending upon the angle of grating 24 with respect to the optical axis of the laser tube and with respect to the plane of output mirror 22, light of a particular, selected wavelength escaping through the Brewster windows 20 of tube 14 will be selectively reflected repeatedly along the axis of the laser tube. This particular wavelength will vary in accordance with the setting of grating 24. Where the wavelength established by the grating corresponds to a transition wavelength of either $^{13}CO_2$ or $^{12}CO_2$, the reflected light will stimulate additional emission of light at the same transition wavelength, resulting in emission of a strong, substantially monochromatic coherent beam at that particular transition wavelength. A portion of that beam is emitted through partially reflective mirror 22 and hence through the output window 30 of the laser on path 42. Wavelength adjustment unit 28 reports the setting of adjusting screws 26, and hence the wavelength of the light emitted by laser 10, to control unit 90.

The laser is initially set to emit at a $^{13}CO_2$ transition wavelength. The light emitted by laser 10 is transmitted along the first path 42 to partially reflective mirror 44. A fixed portion of the light impinging upon mirror 44 passes to power meter 48. The power meter converts this portion of the light into an electrical signal proportional to the power of the laser beam, which signal is transmitted to the control and calculation computer 90. Computer 90 controls the power of the beam by controlling the power applied to the laser discharge via the laser discharge power source 32 (FIG. 2). The major portion of the laser beam passes along path 46, via mirror 50 into chopper 54, where the beam is interrupted at a preselected chopping frequency. The chopper is arranged so that on each chopping cycle, the beam is interrupted and uninterrupted for approximately equal periods, i.e., so that the beam exiting through the chopper outlet 56 on path 57 has about a 50 percent on, 50 percent off duty cycle and switches back and forth between the on and off conditions at the preselected chopping frequency.

The alternating, on and off light beam passing from the chopper enters the interior of cell 60 through window 62, passes through the discharge within the cell and through window 64, where it is reflected back into the cell by mirror 66. The light passing through the electrical discharge within chamber 60 interacts with the excited $^{13}CO_2$ molecules in the discharge. Where the light is at a particular wavelength corresponding to a transition of a $^{13}CO_2$ molecule between a relatively high energy excited state and a lower state such as a lower energy excited state or the ground state, the light will interact with $^{13}CO_2$ molecules in such first or high energy excited state, causing a resonant transition between the high energy excited state and the lower state. The light does not substantially interact with the $^{12}CO_2$ in the discharge within chamber 60.

The transitions induced by the light will alter the distribution of states of the $^{13}CO_2$ molecules within the discharge and hence will alter the electrical impedance of the discharge via the so-called optogalvanic effect. Although the present invention is not limited by any theory of operation, the optogalvanic effect is believed to result from changes in ionization or in the overall electron temperature in the discharge caused by the transitions. Thus, while the laser 10 is emitting light at a transition energy corresponding to a transition energy of a $^{13}CO_2$ excited state, the electrical impedance of the discharge in chamber 60 will vary between first and second values as chopper 54 switches the light beam on and off. The discharge impedance does not change instantaneously when the light beam is switched on or off, but instead requires a short but nonetheless finite rise time to reach equilibrium at the new value. This rise time typically is on the order of a few microseconds. The period of the chopper cycle is selected so that each on period and each off period is substantially longer than the rise time. For example, the chopper frequency may be less than about 500 Hz, typically about 200 to about 350 Hz. The discharge impedance comes to equilibrium at the first value during each on cycle of the chopper and at the second value during each off cycle of the chopper. The difference between the first and second values of the discharge impedance is the optogalvanic signal for the particular $^{13}CO_2$ transition associated with the wavelength of the applied light beam. The changing impedance is reflected as an AC component in the impedance signal delivered by impedance monitoring device 82. This AC component is isolated by lock-in amplifier 84 and passed to control and calculation device 90, where its peak-to-peak value is recorded as the optogalvanic signal.

Under fixed discharge conditions in a given instrument:

$$S_1 = (P_{13})(M_{13})(W_{13}) \qquad (1)$$

where:

$S_{13}$ is the optogalvanic signal for the particular $^{13}CO_2$ transition;

$P_{13}$ is the partial pressure or molecular concentration of $^{13}CO_2$ in the gas within chamber 60;

$W_{13}$ is the power level of the laser beam at the wavelength corresponding to the $^{13}CO_2$ transition; and $M_{13}$ is a proportionality constant which depends upon factors such as the magnitude of the optogalvanic effect for the particular transition, the proportion of $^{13}CO_2$ molecule which is in the active state under the discharge conditions and the configuration of the instrument.

The foregoing relationship applies for values of $W_{13}$ below a saturation level. The saturation level is the level of laser beam power required to trigger the transition in substantially all of the $^{13}CO_2$ which is in the first excited state. Thus, above this saturation power level, further increases in the laser beam power would not increase the optogalvanic signal $S_{13}$.

After the $^{13}CO_2$ optogalvanic signal has been acquired, screws 26 (FIG. 2) are actuated to set the grating 24 to a different angle and thereby tune laser 10 to a wavelength corresponding to a transition of $^{12}CO_2$, so that the laser operates at this $^{12}CO_2$ transition wavelength. The light from the laser corresponding to the $^{12}CO_2$ transition interacts with $^{12}CO_2$ molecules in a particular excited state, but does not interact substantially with $^{13}CO_2$ in cell 60. Once again, the chopper 54 repeatedly interrupts the light beam passing along path 57 into cell 60, so that the impedance of the discharge measured by impedance monitoring device 82 repeatedly fluctuates between first and second values. The difference between these first and second values is the optogalvanic signal for the $^{12}CO_2$ transition. In this case:

$$S_{12} = (P_{12})(M_{12})(W_{12}) \quad (2)$$

where:

$S_{12}$ is the optogalvanic signal for $^{12}CO_2$ transition;

$P_{12}$ is the molecular concentration or partial pressure of $^{12}CO_2$ in the gas inside chamber 60;

$M_{12}$ is a proportionality constant for the particular transition; and $W_{12}$ is the power of the laser beam at the wavelength corresponding to the $^{12}CO_2$ transition, as measured by power meter 48 during operation at this wavelength. The formula applies only for values of the power $W_{12}$ below a saturation level required to trigger transitions of all excited $^{12}CO_2$ molecules in the discharge. Like $S_{13}$, $S_{12}$ appears as the peak-to-peak value of the AC component in the signal from impedance monitoring device 82 at the frequency corresponding to the chopping frequency. This AC component is isolated by lock-in amplifier 86 and passed to the control and calculation unit 90.

The isotopic ratio or ratio of $^{13}CO_2$ to $^{12}CO_2$ in the sample is given by:

$$\frac{(S_{13})(M_{12})(W_{12})}{(S_{12})(M_{13})(W_{13})} = \frac{P_{13}}{P_{12}} = R_{13/12} \quad (3)$$

where $R_{13/12}$ is the ratio of $^{13}CO_2$ to $^{12}CO_2$ in the analyte within cell 60. Stated another way, $$\frac{(S_{13})(W_{12})}{(S_{12})(W_{13})} K = R_{13/12} \quad (4)$$

where K is a calibration constant equal to $M_{12}/M_{13}$, and is fixed for particular $^{13}CO_2$ and $^{12}CO_2$ transitions, instrument configuration and discharge power conditions in cell 60. The value of K can be obtained by calibrating the instrument with a gas of a known value of $R_{13/12}$.

The energy of the $^{12}CO_2$ transition is different from the energy of the $^{13}CO_2$ transition, and hence the wavelength corresponding to the $^{12}CO_2$ transition does not trigger the $^{13}CO_2$ transition or appreciably affect the $^{13}CO_2$. The optogalvanic signal at the $^{12}CO_2$ wavelength is essentially independent of $^{13}CO_2$ concentration. Stated another way, the particular $^{12}CO_2$ and $^{13}CO_2$ transitions used in the system are selected so that the transition energy of the $^{12}CO_2$ transition does not correspond to the transition energy of any $^{13}CO_2$ transition and so that the transition energy of the $^{13}CO_2$ transition employed in the system does not correspond to any $^{12}CO_2$ transition. Also, the particular transition energies and transition wavelengths are selected so that the transition wavelengths differ from transition wavelengths of other gas species present in the system, such as the transition energies of the carrier gases and expected contaminants. For example, where the $CO_2$ in the analyte is derived from a biological source and is contaminated with water, the transition wavelengths should be selected so that they do not correspond to transition wavelengths of water molecules or OH- ions or complexes which may be present in the discharge as a result of the contamination. The methods and apparatus discussed above can provide extraordinarily high sensitivity and low detection limits. Values of the isotopic ratio $R_{13/12}$ as low as about $10^{-4}$ to about $10^{-6}$ can be measured accurately. For work with low values of R, the transition energies selected should provide a high value of $M_{13}$ so as to thereby provide an appreciable value of $S_{13}$ and maximize the signal to noise ratio during measurement of $S_{13}$. The $^{13}CO_2$ transition wavelength at about 11.12 microns is particularly preferred in this case. Likewise, the $^{13}CO_2$ transition beam power level $W_{13}$ should be close to the saturation power level. To assure that the $^{12}CO_2$ signal $S_{12}$ is of comparable magnitude to the $S_{13}$ signal in this situation, transition wavelengths providing a relatively low value of $M_{12}$, and/or a relatively low power $CO_2$ transition beam having a low value of $W_{12}$ may be employed. There are numerous weak transitions of $^{12}CO_2$ providing low values of $M_{12}$. Among these are the transition wavelengths at 10.49, 10.30 and 10.76 microns.

The methods and apparatus discussed above can be varied in numerous ways. In one variant, two separate lasers are employed. Each is operated at one of the transition wavelengths, and each laser beam is passed through a different chopper on route to the sample chamber. The two choppers are operated at different chopping frequencies, so that the two laser beams at the different transition wavelengths are switched on and off at different frequencies. Both of these beams may be applied simultaneously. In this case, the signal from the impedance monitoring device will incorporate two separate AC components at the two separate chopping frequencies. The signal from the impedance monitoring device is fed to two separate lockin amplifiers, one operating at each chopping frequency, so that each lock-in amplifier isolates an AC component at chopping frequency representing the optogalvanic signal for one of the two simultaneously applied wavelengths.

According to further variants, the response of the analyte to the applied light at the different wavelengths can be monitored by monitoring phenomena other than the optogalvanic effect. The interaction of the applied light beam with the gas in the discharge gives rise to mechanical pressure in the discharge. Where the light is chopped at a given frequency, the repeated on and off cycles will produce sound waves in the discharge at the chopping frequency. The magnitude of this optoacoustic effect for light of different wavelengths can be used instead of the magnitude of the optogalvanic effect. The optoacoustic effect, however, generally provides lower sensitivity.

As discussed above, the interaction between the applied light and the excited, isotope-bearing molecules triggers the transition of such molecules between states. By definition, any transition has an associated lower-energy state and an associated higher-energy state. Each transition can operate in a first direction, from the lower-energy state to the higher-energy state, or in a second direction from the higher-energy state to the lower-energy state. Operation in the first direction corresponds to absorption of an incident photon, whereas operation in the second direction corresponds to emission of a photon. The population distribution in the discharge will determine whether operation in the first or second direction is predominant. Thus, under some discharge conditions the predominant response to light of a particular wavelength may be absorption or first-direction operation, whereas under other discharge conditions the predominant response to the same wavelength may be emission or second-direction operation. Either effect will produce an optogalvanic or optoacoustic signal. Where the predominant effect is emission or transition to a lower energy state, the response to the applied light will include emission of further photons at the wavelength corresponding to the transition energy. Thus, the applied light at the wavelength corresponding to the transition energy is amplified by the emissions of the analyte at such wavelength. This effect can be measured and used as an indication of the effect of the light at the different transition wavelengths on the analyte. The apparatus of FIG. 1 can be modified to provide such measurements by substituting a light power meter for mirror 66, by deleting chopper 54 and modifying the discharge power source so as to turn the discharge on and off repeatedly at a selected switching frequency. The added power meter will measure the power of the laser beam after passage through the discharge including the analyte within chamber 60. Comparison of the reading from this added power meter with the discharge on and off will indicate the degree of amplification. This measurement can be repeated for light at the two transition wavelengths associated with the two isotopes.

The transition triggered by the applied light may be referred to as a "primary" transition. In some cases, the primary transition takes the excited, isotope-bearing species to a higher-energy or lower-energy excited state which then decays in a further, "secondary" transition to a second lower energy state. This second lower energy state may be another excited state or the ground state. Each such secondary transition yields a photon at a secondary transition wavelength. The number of such secondary transitions, and hence the amount of light emitted at the secondary transition wavelength, will increase with the number of primary transitions triggered by the applied light. Accordingly, the amount of light emitted by the analyte at the secondary transition wavelength can be used to measure the effect of the incident light on the analyte. Incident light at the first transition wavelength associated with the primary transition of the excited species including one isotope is applied and the response is measured by measuring the resulting emission at the secondary transition wavelength. Light at the second primary transition wavelength associated with the primary transition of the excited species including the other isotope is applied and the resulting secondary emission is monitored. The amplitudes of the secondary emissions resulting from incidence light at the first and second primary transition wavelengths are compared to give a measure of the isotopic ratio in the analyte. The secondary emission may be detected by a conventional photocell detector. Typically, the photocell detector in such an arrangement is provided with a wavelength selective filter arranged to exclude light at the primary transition wavelengths but to admit light at the secondary transition wavelengths. Light at the first and second primary transition wavelengths may be applied sequentially, in which case the photodetector signal will represent secondary emissions from excited species including the two isotopes in sequence. Alternatively, light at the two primary transition wavelengths may be applied simultaneously provided that the light at each primary transition wavelength is chopped or amplitude-modulated at a different frequency. In this case, the signal from the photodetector will include components varying with time at the two different modulation frequencies representing the secondary emissions evoked by the two different primary transition wavelengths. These components can be separated to give separate signals representing the response to each primary transition wavelength.

In the arrangements discussed above, the light applied to the analyte is obtained from one or more lasers having a laser medium including the isotope-bearing species present in the analyte. Thus, in the arrangements discussed above using $CO_2$ as the isotope-bearing species, the applied light is obtained from a single $CO_2$ laser including mixtures of $^{13}CO_2$ and $^{12}CO_2$ or from two separate $CO_2$ lasers including these species. Such arrangements are particularly preferred because the light will be inherently tuned to transition wavelengths of the isotope-bearing species. However, other sources of light may be used provided that the light source yields light at the appropriate transition wavelengths. For example, a tunable dye laser or other form of laser tunable over a continuous range of wavelengths may be employed. The emissions from such a laser may be locked to a transition frequency associated with a particular isotope. For example, a portion of the laser beam may be directed to a reference cell similar to the sample cell discussed above. The reference cell includes a gas mixture incorporating a known sample of the isotope-bearing species, and has an associated discharge power supply. Devices for monitoring the interaction of the laser beam with the discharge in the reference cell, as by monitoring the optogalvanic effect or emissions as discussed above, are also provided. The interaction, such as the optogalvanic signal, is used as a feedback signal to the frequency tuning device of the laser, so that the tuning device adjusts the frequency to the frequency which yields the maximum interaction between the laser beam and the known sample in the reference cell.

Isotope-bearing species other than $CO_2$ may be employed. In general, any multiatomic moiety such as a molecule, multiatomic ion or multiatomic free radical may be employed provided that such moiety is stable enough to survive in reasonable quantities in its excited state under the experimental conditions employed. For example, where an electrical discharge is produced in the analyte, the moiety employed as the isotope-bearing species should be stable enough to survive in reasonable quantities in the electrical discharge. Stable molecules including relatively small numbers of atoms, typically less than 5 atoms and most desirably 3 atoms or less, are preferred as isotope-bearing species. Most preferably, the isotope-bearing species are gaseous at or near room temperature. Methods and apparatus according to the present invention can be used to determine the isotopic composition of essentially any element in an analyte. However, they are particularly well-suited to determination of the isotopic composition of elements selected from the group consisting of carbon, oxygen, nitrogen and hydrogen in the analyte. Thus, the plural isotopes in the isotope-bearing species may be plural isotopes of carbon, of oxygen, of nitrogen, or of hydrogen. Particularly preferred isotope-bearing species for such analysis are oxides of carbon, oxides of nitrogen, $N_2$ and $H_2O$. $CO_2$ can be used as the isotope-bearing species for determination of oxygen isotopic concentration rather than carbon. In this case, the transition wavelengths may be selected to correspond to a transition wavelength of $^{12}C^{16}O_2$ and to a transition wavelength of $^{12}C^{16}O^{18}O$. In this case, a $CO_2$ laser incorporating $^{12}C^{16}O_2$ and $^{12}C^{16}O^{18}O$ can be used to provide the incident light. A similar system can be used with $^{12}C^{16}O_2$ and $^{12}C^{18}O_2$ as the isotope-bearing species. Similarly, the isotopic composition of nitrogen in a sample can be determined using $^{14}N_2$ and one or both of $^{15}N_2$ and $^{15}N^{14}N$ as the isotope-bearing species. A nitrogen laser including these isotope-bearing species can be employed to provide the incident light. The present methods can also be employed to determine the isotopic composition of more than one element in an analyte. In that case, the isotope-bearing species in the analyte would include combinations of isotope-bearing species such as combinations of the preferred species discussed above.

The methods and apparatus can be used to determine the content of an analyte regardless of whether such isotope is stable or radioactive. However, methods which determine the content of stable, non-radioactive isotopes are particularly useful. These methods permit the use of stable isotopes as tracers. Thus, the methods according to the present invention may further include the step of deriving the analyte including the isotope-bearing species from a test subject so that the amounts of the different isotopes in the analyte will vary depending upon a characteristic of the test subject. Thus, the isotopic composition measured according to the steps discussed above will provide an indication of the characteristic of the test subject. The test subject may be a chemical, physical or biological system. For example, the analyte may be obtained by taking a sample from the subject and, if necessary, converting one or more chemical constituents of the test subject into the desired isotope-bearing species. For example, carbon-bearing compounds in a sample may be converted to carbon dioxide. The step of deriving an analyte from a test subject may alternatively or additionally include the step of exposing the test subject to a reagent incorporating a particular isotope used as a tracer, which most preferably is a stable, non-radioactive isotope. For example, where the test subject is a living organism, the test subject can be exposed to the reagent, as by incorporating the reagent in nutrients, air or water in the environment of the test subject. The analyte may be obtained from materials excreted, exuded, or exhaled by the organism or from tissue samples taken from the organism after exposure.

For example, one medical test involves administration of urea labelled with radioactive $^{14}C$ to a patient suspected of having an ulcer such as a duodenal or stomach ulcer. Such patients typically are infected with the microorganism Heliobacter pylori. If that microorganism is present, a substantial portion of the administered $^{14}C$-labelled urea is rapidly converted to $CO_2$ so that the patients breath will contain a substantial proportion of $^{14}CO_2$ after administration of the $^{14}C$-labelled urea. That proportion is conventionally monitored by monitoring the radioactivity of the $^{14}C$ in the breath. According to the present invention, $^{13}C$-labelled urea can be used instead of $^{14}C$-labelled urea. The proportion of $^{13}CO_2$ in the patient's breath may be determined using the methods and apparatus discussed above. Numerous techniques using radioactive isotopes as tracers are known to those skilled in the arts of medicine and biology. Each such technique yields an analyte including the radioactive tracer isotope. The amount of tracer in the analyte is determined by monitoring the amount of radioactivity emitted by the analyte. These techniques can be replicated according to the present invention using stable isotopes as tracers, and the amount of such stable tracer isotopes can be determined using the methods and apparatus discussed above. Among the techniques which may be replicated in this manner are those which involve selective binding, absorption or desorption of biological molecules such as proteins, antigens, antibodies, nucleic acids and the like. Among these techniques are binding assays and competitive binding assays such as radio immunoassay, and radio-labelled lung scanning. The biological or chemical reaction involved in the test may be exactly the same as performed using radioactive isotopes as tracers, except that a stable isotope may be employed and the amount of such isotope in the resulting analyte is determined according to the methods and apparatus discussed above. The term "light" is used in this disclosure as denoting electromagnetic radiation, and is not limited solely to visible light. Thus, depending on the particular transition energies, visible, infrared and ultraviolet wavelengths, as well as other wavelengths, may be used.

As will be appreciated, numerous additional variations and combinations of the features discussed above can be utilized without departing from the present invention as defined by the claims. Accordingly, the foregoing description of the preferred embodiments should be taken by way of illustration rather than by way of limitation of the invention defined by the claims.

The following non-limiting example illustrates certain features of the invention:

EXAMPLE

Research grade (99.995%) bottled carbon dioxide was used as a sample and dry nitrogen as the carrier gas in apparatus as shown in FIG. 1. The gases were mixed in a ratio of 1:19 and admitted to the sample cell to a pressure of 3.61 torr. The laser containing $CO_2$ in an approximate ratio of 1:1 $^{13}CO_2$:$^{12}CO_2$ was first adjusted for the $^{12}CO_2$ P(20) transition at 10.59 microns; the chopper ran at 311 Hz and the laser output was 1.94 W. Subsequently the laser was adjusted to the P(20) line of $^{13}CO_2$ at 11.15 microns providing 0.71 W. The averaged optogalvanic signals from the lock in amplifier yielded a ratio of signal per unit power of 0.0198 (signals of 3650 $\mu V$ and 26.50 $\mu V$). Assuming that the bottled $CO_2$ is representative of natural $CO_2$ in its isotopic makeup (1.108% $^{13}CO_2$) the calibration factor for the measurement is 0.5596.

What is claimed is:

1. A method of determining the isotopic composition of an analyte including isotope-bearing species incorporating a plurality of isotopes comprising the steps of:
   (a) providing said analyte in a condition such that said isotope-bearing species are present in excited states, whereby excited isotope-bearing species incorporating different isotopes will have different transition energies;
   (b) applying radiation to said analyte at plural wavelengths corresponding to said different transition energies, whereby applied radiation at each of said wavelengths will interact selectively with excited isotope-bearing species in said analyte incorporating different ones of said isotopes; and
   (c) monitoring response of said analyte to said applied radiation so as to determine a magnitude of said response for each of said wavelengths, said isotope-bearing species being multiatomic moieties.

2. A method as claimed in claim 1, wherein said multiatomic moieties are molecules including less than 5 atoms.

3. A method as claimed in claim 1 wherein said step of providing said analyte includes the step of providing said analyte in gaseous form.

4. A method as claimed in claim 3 wherein said step of providing said analyte further includes the step of maintaining said gaseous analyte in an electrical discharge.

5. A method as claimed in claim 4 wherein said step of monitoring response of said analyte includes the step of monitoring electrical impedance of said electrical discharge.

6. A method as claimed in claim 5 wherein said step of applying radiation includes the step of periodically varying the amplitude of said radiation and said step of monitoring said electrical impedance includes the step of monitoring a component of said impedance varying in synchronism with said varying amplitude.

7. A method as claimed in claim 1 wherein said step of applying radiation includes the step of operating at least one laser having at least one lasing medium separate from said analyte incorporating said isotope-bearing species.

8. A method as claimed in claim 7 wherein said at least one laser includes a single laser having a lasing medium separate from said analyte incorporating said isotope-bearing species with a plurality of said different isotopes, said step of operating said at least one laser including the step of actuating said single laser to laser at said wavelengths corresponding to said transition frequencies.

9. A method as claimed in claim 8 wherein said step of actuating said single laser includes the step of tuning said single laser to said different wavelengths sequentially.

10. A method as claimed in claim 7 wherein said step of providing said analyte includes the step of providing said analyte in gaseous form.

11. A method as claimed in claim 1 wherein said plural isotopes in said analyte are plural isotopes of one or more elements selected from the group consisting of carbon, oxygen and nitrogen.

12. A method as claimed in claim 11 wherein said isotope-bearing species is selected from the group consisting of oxides of carbon, hydrogen, oxides of nitrogen, $N_2$, $H_2O$ and combinations thereof.

13. A method as claimed in claim 12 wherein said isotope-bearing species is carbon dioxide.

14. A method as claimed in claim 1 wherein said plural isotopes are stable isotopes.

15. A method as claimed in claim 1 wherein said step of applying radiation includes the steps of applying radiation at a wavelength corresponding to a transition energy of a first isotope-bearing species during a first interval and applying radiation at a wavelength corresponding to a transition energy of a second isotope-bearing species during a second interval separate from said first interval, said step of monitoring response of said analyte including the steps of separately determining first and second response magnitudes of said response of said analyte during said first and second intervals respectively, the method further comprising the step of computing said isotopic composition by comparing said first and second response magnitudes.

16. A method as claimed in claim 1 wherein said step of applying radiation includes the steps of applying first radiation at a wavelength corresponding to a transition energy of a first isotope-bearing species so that said first radiation varies in amplitude at a first frequency and applying second radiation at a wavelength corresponding to a transition energy of a second isotope-bearing species so that said second radiation varies in amplitude periodically at a second frequency different from said first frequency, said step of monitoring response of said analyte including the step of determining the magnitudes of first and second components of said response of said analyte varying at said first and second frequencies, the method further comprising the step of computing said isotopic composition by comparing said magnitudes of said first and second components.

* * * * *

UNITED STATES PATENT AND TRADEMARK OFFICE
CERTIFICATE OF CORRECTION

PATENT NO. : 5,394,236
DATED : February 28, 1995
INVENTOR(S) : Daniel E. Murnick It is certified that error appears in the above-identified patent and that said Letters Patent is hereby corrected as shown below:

Column 10, line 54, change "$S_1$" to read -- $S_{13}$ --.

Column 12, line 51, change "lockin" to read -- lock-in --.

Signed and Sealed this

Twentieth Day of June, 1995

Attest:

BRUCE LEHMAN

*Attesting Officer*    *Commissioner of Patents and Trademarks*